United States Patent [19]
Hirai et al.

[11] Patent Number: 6,034,107
[45] Date of Patent: Mar. 7, 2000

[54] 5-SUBSTITUTED PICOLINIC ACID COMPOUNDS AND THEIR PRODUCTION PROCESS

[75] Inventors: Hideo Hirai; Katsuomi Ichikawa; Nakao Kojima; Hiroyuki Nishida; Kunio Satake; Nobuji Yoshikawa, all of Aichi-ken, Japan

[73] Assignee: Pfizer Inc., New York, N.Y.

[21] Appl. No.: 09/178,949

[22] Filed: Oct. 26, 1998

[51] Int. Cl.⁷ .................. A61K 31/44; C07D 401/04
[52] U.S. Cl. ................ 514/340; 514/344; 514/354; 514/356; 546/326; 546/268.4; 546/323; 546/286
[58] Field of Search ................ 546/326, 268.4, 546/323, 286; 514/340, 344, 354, 356

[56] References Cited

FOREIGN PATENT DOCUMENTS 11222480  8/1999  Japan .

*Primary Examiner*—Jane Fan
*Attorney, Agent, or Firm*—Peter C. Richardson; Gregg C. Benson; Robert T. Ronau

[57] ABSTRACT

The present invention provides novel 5-substituted picolinic acid compounds of formula (I) or a pharmaceutically acceptable salt thereof:

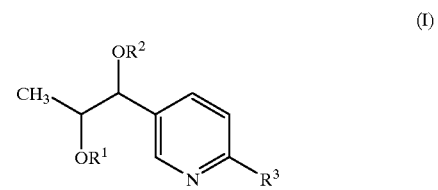

(I)

wherein $R^1$ and $R^2$ are independently H, $C_2$–$C_6$ acyl or halo-substituted benzoyl; and $R^3$ is —C(O)O—$C_1$–$C_6$ alkyl, C(O)OH, CN, $CONH_2$, $CONHCH_3$, $CON(CH_3)_2$, 1-methyltetrazole or 2-methyltetrazole, with the proviso that when $R_2$ is acetyl and $R^3$ is methoxycarbonyl, $R^1$ is not H; and that when $R^3$ is CN, $CONH_2$, $CONHCH_3$, $CON(CH_3)_2$, 1-methyltetrazole or 2-methyltetrazole, $R^1$ and $R^2$ are H.

The present invention also relates to a pharmaceutical composition comprising compound of the present invention, which is useful in the treatment of IL-1 and TNF mediated diseases or the like.

The present invention further relates to a process for producing the compounds of the formula (I).

8 Claims, No Drawings

5-SUBSTITUTED PICOLINIC ACID COMPOUNDS AND THEIR PRODUCTION PROCESS

TECHNICAL FIELD

This invention relates to novel 5-substituted picolinic acid compounds, and particularly to novel 5-substituted picolinic acid compounds produced by fermentation of a fungus Marasmiellus sp., which has been deposited as FERM BP-5735. This invention also relates to processes for producing the 5-substituted picolinic acid compounds, and a pharmaceutical composition comprising the same, which is useful in the treatment of IL-1 and TNF mediated diseases.

BACKGROUND ART

Interleukin-1 (IL-1) and tumor necrosis factor (TNF) are biological substances produced by a variety of cells, such as monocytes or macrophages. IL-1 and TNF have been demonstrated to mediate a variety of biological activities thought to be important in immunoregulation and other physiological conditions such as inflammation.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes (T. Mandrup-Poulsen et al., Allergy, 1985, 40, 424). The only IL-1 blocker available today is the natural IL-1 receptor antagonist (IL-1RA), which is easily metabolized in the bloodstream with a very short half-life (E. V. Granowitz et al., Cytokine, 1992, 4, 353). Thus, active research has been carried out to develop stable, long-acting agents which can be taken by oral administration or by parenteral injections rather than by intravenous infusion, which is required for IL-1RA. A number of compounds as IL-1 receptor antagonists, IL-1 biosynthesis inhibitors, and IL-1 converting enzyme inhibitors have been known (C. C. George et al., Exp. Opin. Ther. Paten, 1996, 6 (1), 41).

Excessive or unregulated TNF production has also been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, acquired immunodeficiency syndrome (AIDS), AIDS related complex (ARC), keloid formation, scar tissue formation, Crohn's disease, ulcerative colitis, or pyresis. Although significant progress in developing potent TNF modulators has been achieved through the use of recombinantly derived proteins including monoclonal antibodies and soluble receptors, the development of biosynthesis inhibitors and receptor antagonists has been less successful. Recently a number of small molecule TNF modulators have been claimed. Most of them which specifically inhibit TNF production do so by increasing intracellular cyclic adenosine monophosphate (cAMP) which ultimately blocks TNF gene expression (Y. KATAKAMI et al., Immunology, 1988, 64, 719). The most important of these compounds are the rolipram and pentoxifylline-related phosphodiesterase IV (PDE IV) inhibitors which are being pursued by a number of pharmaceutical companies (A. BADGER et al., Circul. Shock, 1994, 44, 188). The ability of thalidomide to block TNF production contributes to its therapeutic properties in humans (E. P. SAMPAIO et al., J. Exp. Med, 1991, 73, 699). Recent studies suggest that cell-associated TNF may be necessary for normal host defense mechanisms. This finding has added to the excitement concerning the identification of a unique metalloproteinase enzyme which is responsible for the proteolytic processing of TNF. Inhibitors of matrix metalloproteinase-related enzyme have appeared (K. M. MOHLER et al., Nature, 1994,370, 218).

Inhibitors of interleukin 1, 6 and 8 and TNF are described in PCT application US94/07969 which was published on Jan. 26 1995. The inhibitors of TNF are also described in PCT application US94/04950 which was published on Nov. 24 1994. Substituted picolinic acid compounds have been known to be produced by fungus. These include phenopicolinic acid (5-(4-hydroxylbenzyl)picolinic acid) (T. Nakamura et al., J. Antibiotics, 27:477-, 1975), fusaric acid (5-butylpicolinic acid)(H. Hidaka et al., J.Antibiotics, 22:228-, 1969), and fusarinolic acid (K. Steiner et al., Helv. Chim. Acta, 54:845-, 1971).

The object of the present invention is to provide novel 5-substituted picolinic acid compounds having an excellent activities for TNF and/or IL-1 biosynthesis inhibition and a pharmaceutically composition comprising the same. Another object is to provide processes for producing the novel 5-substituted picolinic acid compounds.

BRIEF DISCLOSURE OF THE INVENTION

Accordingly, the present invention provides novel 5-substituted picolinic acid compounds of formula (I):

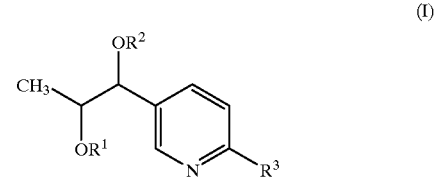

(I)

or a pharmaceutically acceptable salt thereof,
wherein $R^1$ and $R^2$ are independently H, $C_2$–$C_6$ acyl or halo-substituted benzoyl; and $R^3$ is —C(O)O—$C_1$–$C_6$ alkyl, C(O)OH, CN, $CONH_2$, $CONHCH_3$, $CON(CH_3)_2$, 1-methyltetrazole or 2-methyltetrazole, with the proviso that when $R^2$ is acetyl and $R^3$ is methoxycarbonyl, $R^1$ is not H; and that when $R^3$ is CN, $CONH_2$, $CONHCH_3$, $CON(CH_3)_2$, 1-methyltetrazole or 2-methyltetrazole, $R^1$ and $R^2$ are H.

Preferred compounds of this invention are those of formula (I) shown above, wherein $R^3$ is —C(O)O—$C_1$–$C_6$ alkyl or C(O)OH, with the proviso that when $R^2$ is acetyl and $R^3$ is methoxycarbonyl, $R^1$ is not H.

The present invention also provides a culture of Marasmiellus sp. FERM BP-5735, which is capable of producing the 5-substituted picolinic acid compounds, especially those of formula (I) wherein wherein $R^1$ and $R^2$ are H, and $R^3$ is methoxycarbonyl (methyl 5-(1,2-dihydroxypropyl)-2-pyridinecarboxylate), or $R^1$ is acetyl, $R^2$ is H, and $R^3$ is methoxycarbonyl (methyl 5-(1-acetoxy-2-hydroxypropyl)-2-pyridinecarboxylate).

Further, the present invention provides a process for producing the 5-substituted picolinic acid compounds of formula (I), which comprises cultivating a microorganism having identifying characteristics of Morasmiellus sp., FERM BP-5735, or a mutant or recombinant form thereof.

The present invention further provides a process comprising additional steps of isolating the 5-substituted picolinic acid compounds from the fermentation broth and chemically modifying the isolated compounds.

Also, the present invention provides a pharmaceutical composition for use in the treatment of IL-1 and/or TNF mediated diseases, which comprises the 5-substituted picolinic acid compounds of formula (I) wherein $R^1$ and $R^2$ are H; and $R^3$ is methoxycarbonyl (methyl 5-(1,2-dihydroxypropyl)-2-pyridinecarboxylate); $R^1$ is acetyl; $R^2$ is H; and $R^3$ is methoxycarbonyl (methyl 5-(1-acetoxy-2-hydroxypropyl)-2-pyridinecarboxylate); $R^1$ and $R^2$ are H; and $R^3$ is C(O)OH (5-(1,2-dihydroxypropyl)-2-pyridinecarboxylic acid); or $R^1$ and $R^2$ are acetyl; and $R^3$ is methoxycarbonyl (methyl 5-(1,2-diacetoxypropyl)-2-pyridinecarboxylate); or pharmaceutically acceptable salt thereof in an amount effective in such treatments, and a pharmaceutically acceptable carrier.

Also, the present invention provides a method for the treatment of IL-1 and/or TNF mediated diseases, which comprises administering to said subject an antiinflammation amount of the compound of formula (I) wherein $R^1$ and $R^2$ are H; and $R^3$ is methoxycarbonyl (methyl 5-(1,2-dihydroxypropyl)-2-pyridinecarboxylate); $R^1$ is acetyl; $R^2$ is H; and $R^3$ is methoxycarbonyl (methyl 5-(1-acetoxy-2-hydroxypropyl)-2-pyridinecarboxylate); $R^1$ and $R^2$ are H; and $R^3$ is C(O)OH (5-(1,2-dihydroxypropyl)-2-pyridinecarboxylic acid); or $R^1$ and $R^2$ are acetyl; and $R^3$ is methoxycarbonyl (methyl 5-(1,2-diacetoxypropyl)-2-pyridinecarboxylate); and a pharmaceutically acceptable carrier.

DETAILED DESCRIPTION OF THE INVENTION

The microorganism used in this invention is a strain of Marasmiellus sp. which was identified by and obtained from University of Tennessee. It was deposited under the accession number FERM BP-5735 to National Institute of Bioscience and Human-Technology, Agency of Industrial Science and Technology (located at 1-3 Higashi 1-chome, Tsukuba, Ibaraki 305, Japan) under the Budapest Treaty on Oct. 29, 1996. The taxonomical properties of the genus Marasmiellus have been reported by Singer, R. (in *The Agaricales in modern taxonomy*, 320–328, 1986).

In this invention, a mutant or recombinant form of FERM BP-5735 having the ability to produce the novel 5-substituted picolinic acid compounds of formula (I) can be also used. The mutant or recombinant form may be obtained by spontaneous mutation, artificial mutation with ultraviolet radiation, or treatment with mutagen such as N-methyl-N'-nitro-N-nitrosoguanidine or ethyl methanesulfonate, or a cell technology method such as protoplast fusion, gene manipulation or the like, according to well-known methods.

According to the present invention, the novel 5-substituted picolinic acid compounds of formula (I) may be produced by aerobic fermentation of FERM BP-5735, or a mutant or recombinant form thereof, under conditions similar to those generally employed to produce bioactive compounds by fermentation.

FERM BP-5735, or a mutant or recombinant form thereof, is usually fermented under submerged aerobic conditions with agitation at a temperature of 20 to 40° C. for 1 to 20 days, which may be varied according to fermentation conditions. Cultivation of FERM BP-5735 to produce said 5-substituted picolinic acid compounds of formula (I) preferably takes place in aqueous nutrient media at a temperature of 25 to 35° C. for 10 to 15 days. The pH of medium may be adjusted in the range from 4.0 to 9.0, preferably from 5.5 to 7.0.

Nutrient media useful for fermentation include a source of assimilable carbon such as sugars, starches and glycerol; a source of organic nitrogen such as casein, enzymatic digest of casein, soybean meal, cotton seed meal, peanut meal, wheat gluten, soy flour, meat extract and fish meal; a source of growth substances such as mineral salts, sodium chloride and calcium carbonate; and trace elements such as iron, magnesium, copper, zinc, cobalt and manganese. If excessive foaming is encountered during fermentation, antifoam agents such as polypropylene glycols or silicones may be added to the fermentation medium.

Aeration of the medium in fermentors for submerged growth is maintained at 10 to 200%, preferably at 50 to 150% volumes of sterile air per volume of the medium per minutes. The rate of agitation depends on the type of agitator employed. A shake flask is usually run at 150 to 250 rpm whereas a fermentor is usually run at 300 to 2,000 rpm. Aseptic conditions must, of course, be maintained through the transfer of the organism and throughout its growth.

The 5-substituted picolinic acid compounds thus produced may be isolated by standard techniques such as extraction and various chromatographic techniques.

As 5-substituted picolinic acid compounds of this invention, a compound of formula (I) wherein $R^1$ and $R^2$ are H, and $R^3$ is methoxycarbonyl (methyl 5-(1,2-dihydroxypropyl)-2-pyridinecarboxylate); and a compound of formula (I) wherein $R^1$ is acetyl, $R^2$ is H, and $R^3$ is methoxycarbonyl (methyl 5-(1-acetoxy-2-hydroxypropyl)-2-pyridinecarboxylate) were isolated in a substantially pure form from the fermentation mixture. As 5-substituted picolinic acid compounds of this invention, there were synthesized 5-(1,2-dihydroxypropyl)-2-pyridinecarboxylic acid, methyl 5-(1,2-diacetoxypropyl)-2-pyridinecarboxylate, methyl 5-(1,2-di-p-bromobenzoyloxypropyl)-2-pyridinecarboxylate, 5-(1,2-dihydroxypropyl)-2-pyridinecarboxamide, 5-(1,2-dihydroxypropyl)-N,N-dimethyl-2-pyridinecarboxamide, 5-(1,2-dihydroxypropyl)-2-pyridinecarbonitrile, 5-(1,2-dihydroxypropyl)-2-(2-methyl-2H-1,2,3,4-tetrazol-5-yl)pyridine and 5-(1, 2-dihydroxypropyl)-2-(1-methyl-1H-1,2,3,4-tetrazol-5-yl)pyridine from methyl 5-(1,2-dihydroxypropyl)-2-pyridinecarboxylate by chemical modification. These compounds were identified by various spectroscopic techniques such as UV spectrophotometry, NMR and mass spectrometries, and the results will be shown in the section for working examples.

The compounds of formula (I) wherein $R^1$ and $R^2$ are an acyl group can be prepared by acylation of methyl 5-(1,2-dihydroxypropyl)-2-pyridinecarboxylate, and the compounds of formula (I) wherein $R^3$ is alkoxycarbonyl can be prepared by alkylation of demethyl methyl 5-(1,2-dihydroxypropyl)-2-pyridinecarboxylate using suitable acylation and alkylating agents under suitable conditions known to those skilled in the art.

Preferred compounds of this invention include those of formula (I), wherein
$R^1$ and $R^2$ are H; and $R^3$ is methoxycarbonyl (methyl 5-(1,2-dihydroxypropyl)-2-pyridinecarboxylate);
$R^1$ is acetyl; $R^2$ is H; and $R^3$ is methoxycarbonyl (methyl 5-(1-acetoxy-2-hydroxypropyl)-2-pyridinecarboxylate);

$R^1$ and $R^2$ are H; and $R^3$ is C(O)OH (5-(1,2-dihydroxypropyl)-2-pyridinecarboxylic acid);
$R^1$ and $R^2$ are acetyl; and $R^3$ is methoxycarbonyl (methyl 5-(1,2-diacetoxypropyl)-2-pyridinecarboxylate); and
$R^1$ and $R^2$ are p-bromobenzoyl; and $R^3$ is methoxycarbonyl (methyl 5-(1,2-di-p-bromobenzoyloxypropyl)-2-pyridinecarboxylate).

Preferred compounds of this invention also include those of the formula (I), wherein
$R^1$ and $R^2$ are H, and $R^3$ is CN(5-(1,2-dihydroxypropyl)-2-pyridinecarbonitrile);
$R^1$ and $R^2$ are H, and $R^3$ is $CONH_2$ (5-(1,2-dihydroxypropyl)-2-pyridinecarboxamide);
$R^1$ and $R^2$ are H, and $R^3$ is $CONHCH_3$ (5-(1,2-dihydroxypropyl)-N-methyl-2-pyridinecarboxamide);
$R^1$ and R2 are H, and $R^3$ is $CON(CH_3)_2$ (5-(1,2-dihydroxypropyl)-N,N-dimethyl-2-pyridinecarboxamide);
$R^1$ and $R^2$ are H, and $R^3$ is 1-methyltetrazole (5-(1, 2-dihydroxypropyl)-2-(1-methyl-1H-1,2,3,4-tetrazol-5-yl)pyridine); and
$R^1$ and $R^2$ are H, and $R^3$ is 2-methyltetrazole (5-(1, 2-dihydroxypropyl)-2-(2-methyl-2H-1,2,3,4-tetrazol-5-yl)pyridine).

More preferred compounds include a compound of formula (I), wherein $R^1$ and $R^2$ are H; and $R^3$ is methoxycarbonyl (methyl 5-(1,2-dihydroxypropyl)-2-pyridinecarboxylate);
$R^1$ is acetyl; $R^2$ is H; and $R^3$ is methoxycarbonyl (methyl 5-(1-acetoxy-2-hydroxypropyl)- 2-pyridinecarboxylate);
$R^1$ and $R^2$ are H; and $R^3$ is C(O)OH (5-(1,2-dihydroxypropyl)-2-pyridinecarboxylic acid); and
$R^1$ and $R^2$ are acetyl; and $R^3$ is methoxycarbonyl (methyl 5-(1,2-diacetoxypropyl)-2-pyridinecarboxylate).

Further preferred compounds of this invention also include those of formula (I) wherein
$R^1$ and $R^2$ are H, $R^3$ is $CONH_2$ (5-(1,2-dihydroxypropyl)-2-pyridinecarboxamide)
$R^1$ and $R^2$ are H, $R^3$ is $CON(CH_3)_2$ (5-(1,2-dihydroxypropyl)-N,N-dimethyl-2-pyridinecarboxamide)
$R^1$ and $R^2$ are H, $R^3$ is CN (5-(1,2-dihydroxypropyl)-2-pyridinecarbonitrile)
$R^1$ and $R^2$ are H, $R^3$ is 1-methyltetrazole (5-(1, 2-dihydroxypropyl)-2-(2-methyl-2H-1,2,3,4-tetrazol-5-yl)pyridine) and
$R^1$ and $R^2$ are H, $R^3$ is 2-methyltetrazole (5-(1, 2-dihydroxypropyl)-2-(1-methyl-1H-1,2,3,4-tetrazol-5-yl)pyridine).

The IL-1 and TNF biosynthesis inhibitory activities of the above-mentioned 5-substituted picolinic acid compounds, methyl 5-(1,2-dihydroxypropyl)-2-pyridinecarboxylate, (methyl 5-(1-acetoxy-2-hydroxypropyl)-2-pyridinecarboxylate, 5-(1,2-dihydroxypropyl)-2-pyridinecarboxylic acid , methyl 5-(1,2-diacetoxypropyl)-2-pyridinecarboxylate, methyl 5-(1,2-di-p-bromobenzoyloxypropyl)-2-pyridinecarboxylate, 5-(1,2-dihydroxypropyl)-2-pyridinecarboxamide, 5-(1,2-dihydroxypropyl)-N,N-dimethyl-2-pyridinecarboxamide, 5-(1,2-dihydroxypropyl)-2-pyridinecarbonitrile, 5-(1, 2-dihydroxypropyl)-2-(2-methyl-2H-1,2,3,4-tetrazol-5-yl)pyridine and 5-(1, 2-dihydroxypropyl)-2-(1-methyl-1H-1,2, 3,4-tetrazol-5-yl)pyridine), were measured by the standard in vitro protocol described below. These compounds were found to have the IL-1 and TNF biosynthesis inhibitory activities.

TNF bioassay
Heparinised human whole blood diluted four-fold with RPMI medium was incubated with 10 $\mu$g/ml of Lipopolysaccharide (LPS) in the presence of various concentrations of samples at 37° C. in a humidified atmosphere containing 5% $CO_2$ for 4 h. The TNF titer in the supernatants was determined with L929 cells which were destroyed by TNF quantitatively. L929 cells ($2.5 \times 10^4$ cells) in 90 $\mu$l of E-MEM medium containing 1% fetal calf serum and 0.5 $\mu$g/ml of actinomycin D were placed in wells of 96-well microplates (flat-bottom). Ten $\mu$l of the supernatants was added to each well and incubated at 37° C. in a humidified atmosphere containing 5% $CO_2$. After 18 h, the plates were rinsed with 0.9% sterile saline and stained for 10 min with 0.4% crystal violet in MeOH. The plates were washed with distilled water and were dried by air. Fifty $\mu$l of methanol was added to each well to elute the crystal violet, and the plates were read on a microplate reader (model 3550, BIO-RAD) at 595 nm. TNF production inhibitory activity is calculated by the formula:

$$\text{Inhibition (\%)} = \left\{ 1 - \frac{[A_{595}\text{Sample} - A_{595}\text{Blank}]}{[A_{595}\text{Control} - A_{595}\text{Blank}]} \right\} \times 100$$

IL-1 bioassay
The supernatants prepared by the same method as TNF bioassay were analyzed IL-1 titer by commercially available specific ELISA system. The plates were read on a microplate reader (model 3550, BIO-RAD) at 490 nm. IL-1 production inhibitory activity is calculated by the formula:

$$\text{Inhibition (\%)} = \left\{ 1 - \frac{[A_{490}\text{Sample} - A_{490}\text{Blank}]}{[A_{490}\text{Control} - A_{490}\text{Blank}]} \right\} \times 100$$

The pharmaceutically acceptable salts of methyl 5-(1,2-dihydroxypropyl)-2-pyridinecarboxylate, methyl 5-(1-acetoxy-2-hydroxypropyl)-2-pyridinecarboxylate, 5-(1,2-dihydroxypropyl)-2-pyridinecarboxylic acid, methyl 5-(1,2-diacetoxypropyl)-2-pyridinecarboxylate and methyl 5-(1,2-di-p-bromobenzoyloxypropyl)-2-pyridinecarboxylate are prepared in a conventional manner by treating a solution or suspension of the compound with about one chemical equivalent of a pharmaceutically acceptable acid. Conventional concentration and recrystallization techniques are employed in isolating the salts.

Administration
The 5-substituted picolinic acid compounds of formula (I) a pharmaceutically acceptable salt are useful in the treatment of inflammation or the like. The 5-substituted picolinic acid compounds of formula (I) and a pharmaceutically acceptable salt may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the 5-substituted picolinic acid compounds of formula (I) and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia.

Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredients therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the 5-substituted picolinic acid compounds of formula (I) and a pharmaceutically acceptable salt in sesame or peanut oil, aqueous propylene glycol, or in sterile aqueous solution may be employed. Such aqueous solutions should be suitable buffered if necessary and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

Additionally, the 5-substituted picolinic acid compounds of formula (I) and a pharmaceutically acceptable salt may be administered topically when treating conditions of the skin and this may be done by way of creams, jellies, gels, pastes, and ointments, in accordance with standard pharmaceutical practice.

In general, the 5-substituted picolinic acid compounds of formula (I) or its pharmaceutically acceptable salt are present in the above dosage forms at concentration levels ranging 5 to 70% by weight, preferably 10 to 50% by weight.

In general, a therapeutically effective daily dose for the active compound will range from 0.01 to 100 mg/kg, generally from about 1 to about 5 mg/kg As is generally known, the effective dosage for the active compound depends on the intended route of administration and other factors such as age and weight of the patient, as generally known to a physician. The dosage also depends on the illness to be treated.

EXAMPLES

The present invention is illustrated by the following examples. However, it should be understood that the invention is not limited to the specific details of these examples. Spectral and physico-chemical data were obtained on the following instruments: IR, Shimadzu IR-470; UV, JASCO Ubest-30; Optical rotations, JASCO DIP-370 with a 5 cm cell; NMR, JEOL JNM-GX270 equipped with a LSI-11/73 host computer, TH-5 tunable probe and version 1.6 software; EI-MS, Hitachi M-80 with a direct inlet module; and FAB-MS, JEOL JMS-700. The peak shapes are denoted as follows: s (singlet), d (doublet), t (triplet), q (quartet), m (multiplet) and br (broad). FAB-MS spectra were measured using glycerol matrix.

Example One

Fermentation of Marasmiellus sp.
(FERM BP-5735)

Cells from a 10- to 21-day-old petri dish of Marasmiellus sp. FERM BP-5735 grown on malt agar medium (malt extract 2.5% and agar 1.5%) were harvested and suspended in 2 ml sterile water. This suspension was used to inoculate two 500-ml flasks containing 100 ml of Medium-1 (glucose 2%, malt extract 2%, yeast extract 0.18%, maltose 0.24% and agar 0.1%). The flasks were shaken at 26° C. for 7 days on a rotary shaker with 7-cm throw at 220 rpm, to obtain a seed culture. The seed culture was used to inoculate forty 500-ml flasks containing 100 ml of Medium-2 (potato dextrose broth 2.4%). These flasks were shaken at 26° C. for 14 days on a rotary shaker with 7-cm throw at 250 rpm.

Extraction and Isolation

The fermentation broth (3 l) was filtered after the addition of 2 l of ethanol. The filtrate was concentrated to aqueous solution (1 l), which was then extracted 3 times with each of 1 l of n-butanol. The extract was evaporated to afford an oily residue. The oily residue (3.5 g) was applied to a Shephadex LH-20 column (40×500 mm, Pharmacia trademark) and eluted with methanol. The active fractions applied to a YMC-pack ODS AM-343 column (20×250 mm, Yamamura trademark) and eluted with methanol—water (15:85 to 70:30) for 45 min at a flow rate of 10 ml/min. The detection was made by UV absorbance at 220 nm. The eluted peaks showing activity were collected to yield the compounds methyl 5-(1,2-dihydroxypropyl)-2-pyridinecarboxylate (76.7 mg) and methyl 5-(1-acetoxy-2-hydroxypropyl)-2-pyridinecarboxylate (10.2 mg).

HPLC Analysis

Analytical HPLC of methyl 5-(1,2-dihydroxypropyl)-2-pyridinecarboxylate and methyl 5-(1-acetoxy-2-hydroxypropyl)-2-pyridinecarboxylate was performed using a YMC-pack ODS AM-312 column (6.0×150 mm, Yamamura trademark) and eluted with methanol—water (20:80 to 70:30) for 10 min and continuatively to MeOH for 5 min at a flow rate of 0.8 ml/min. The retention times (min) were methyl 5-(1,2-dihydroxypropyl)-2-pyridinecarboxylate (7.7) and methyl 5-(1-acetoxy-2-hydroxypropyl)-2-pyridinecarboxylate (10.9).

Characterization

The physico-chemical properties and spectral data of methyl 5-(1,2-dihydroxypropyl)-2-pyridinecarboxylate and methyl 5-(1-acetoxy-2-hydroxypropyl)-2-pyridinecarboxylate were as follows:

methyl 5-(1,2-dihydroxypropyl)-2-pyridinecarboxylate: white amorphous powder; molecular formula $C_{10}H_{13}NO_4$; LRFAB-MS m/z 212 [M+H]$^+$; HRFAB-MS m/z 212.0940 (calcd. for $C_{10}H_{14}NO_4$, 212.0923); $[\alpha]_D^{24}$ +20.0° (c 0.13, MeOH); UV $1_{max}$ (MeOH) nm (e) 230 (9,500), 270 (5,800); IR $\gamma_{max}$ (KBr) cm$^{-1}$ 3325, 1736, 1437, 1309, 1257, 1122, 1089, 1028, 1001, 817, 709; $^1$H NMR(CD$_3$OD) δ 8.66 (1H, d, J=1.9 Hz), 8.12 (1H, d, J=8.1 Hz), 7.99 (1H, dd, J=8.1 and 1.9 Hz), 4.55 (1H, d, J=5.9 Hz), 3.96 (3H, s), 3.86 (1H, dq, J=6.2 and 5.9 Hz), 1.17 (3H, d, J=6.2 Hz); $^{13}$C NMR (CD$_3$OD) d 167.39 (s), 150.60 (d), 148.20 (s), 144.80 (s), 138.57 (d), 126.57 (d), 77.49 (d), 72.79 (d), 53.95 (q), 19.95 (q).

methyl 5-(1-acetoxy-2-hydroxypropyl)-2-pyridinecarboxylate: white amorphous powder; molecular formula $C_{12}H_{15}NO_5$; LRFAB-MS m/z 254 [M+H]$^+$; HRFAB-MS m/z 254.1051 (calcd. for $C_{12}H_{16}NO_5$, 254.1028); $[\alpha]_D^{24}$ +27.1° (c 0.17, MeOH); UV $1_{max}$ (MeOH) nm (e) 230 (8,200), 270 (4,400); IR $\gamma_{max}$ (KBr) cm$^{-1}$ 3465, 1732, 1435, 1370, 1309, 1239, 1120, 1058, 813, 785, 712; $^1$H-NMR (CD$_3$OD) δ 8.67 (1H, d, J=1.6 Hz), 8.13 (1H, d, J=8.1 Hz), 8.01 (1H, dd, J=8.1 and 1.6 Hz), 5.03 (1H, dt, J=6.2 and 5.4 Hz), 4.82 (1H, d, J=5.4 Hz), 3.97 (3H, s), 1.95 (3H, s), 1.20 (3H, d, J=6.2 Hz).

Example Two

Preparation of 5-(1,2-dihydroxypropyl)-2-pyridinecarboxylic acid

To a solution of methyl 5-(1,2-dihydroxypropyl)-2-pyridinecarboxylate (5 mg) in water (0.1 ml), 1N lithium hydroxide (50 μl) was added at room temperature. After stirring for 1 hour at room temperature, the reaction mixture was neutrized with 1N HCl. The solution was applied to a Diaion HP20 (Mitsubishikasei trademark) column and eluted with methanol-water (1:1) to give 5-(1,2-dihydroxypropyl)-2-pyridinecarboxylic acid: white amorphous powder; molecular formula $C_9H_{11}NO_4$; LRFAB-MS m/z 196 [M−H]$^−$; $^1$H-NMR (D$_3$O) δ 8.74 (1H, d, J=2.2 Hz), 8.47 (1H, d, J=8.1 Hz), 8.28 (1H, dd, J=8.1 and 2.2 Hz), 4.88 (1H, d,J=4.3 Hz), 4.12 (1H, dq, J=6.5 and 4.3 Hz), 1.21 (3H, d,J=6.5 Hz).

Example Three

Preparation of methyl 5-(1,2-diacetoxypropyl)-2-pyridinecarboxylate

To a solution of methyl 5-(1,2-dihydroxypropyl)-2-pyridinecarboxylate (6 mg) in pyridine (0.1 ml), acetic anhydride (50 μl) was added at room temperature. After stirring for 1 hour at room temperature, the reaction mixture was evaporated under N$_2$ gas. The residue was applied to a silica gel plate (Kiesselgel GF$_{254}$, 10×10 cm, Merck trademark) and developed with chloroform-methanol (95:5) to give methyl 5-(1,2-diacetoxypropyl)-2-pyridinecarboxylate: white amorphous powder; molecular formula $C_{14}H_{17}NO_6$; LRFAB-MS m/z 296 [M+H]$^+$; $^1$H-NMR (CDCl$_3$) δ 8.68 (1H, d, J=2.2 Hz), 8.16 (1H, d, J=8.1 Hz), 8.03 (1H, dd, J=8.1 and 2.2 Hz), 5.95 (1H, d, J=4.3 Hz), 5.28 (1H, dq, J=6.5 and 4.3 Hz), 3.97 (3H, s), 2.12 (3H, s), 1.99 (3H, s), 1.18 (3H, d,J=6.5 Hz).

Example Four

Preparation of methyl 5-(1,2-di-p-bromobenzoyloxypropyl)-2-pyridinecarboxylate

To a solution of methyl 5-(1,2-dihydroxypropyl)-2-pyridinecarboxylate (4.1 mg) and a catalic amount of 4-N,N-dimethylaminopyridine in pyridine (1 ml), p-bromobenzoyl chloride (10 mg) was added at room temperature. After stirring at 90° C. for 3 days, the reaction mixture was evaporated under N$_2$ gas. The residue was applied to a silica gel plate (Kiesselgel GF$_{254}$, 10×10 cm, Merck trademark) and developed with chloroform-methanol (95:5) to give 1.03 mg of methyl 5-(1,2-di-p-bromobenzoyloxypropyl)-2-pyridinecarboxylate: white amorphous powder; molecular formula $C_{24}H_{19}Br_2NO_6$; LREI-MS m/z 577 [M]$^+$; $^1$H-NMR (CDCl$_3$) δ 8.88 (1H, d, J=2.0 Hz), 8.16 (1H, d, J=8.4 Hz), 7.94 (1H, dd, J=8.4 and 2.2 Hz), 7.89 (2H, d, J=8.4 Hz), 7.80 (2H, d, J=8.4 Hz), 7.61 (2H, d, J=8.4 Hz), 7.58 (2H, d, J=8.4 Hz), 6.27 (1H, d, J=4.4 Hz), 5.68 (1H, dq, J=6.6 and 4.4 Hz), 4.01 (3H, s), 1.41 (3H, d, J=6.6 Hz).

Example Five

Preparation of 5-(1,2-dihydroxypropyl)-2-pyridinecarboxamide

A homogeneous mixture of methyl 5-(1,2-dihydroxypropyl)-2-pyridinecarboxylate (70.0 mg, 0.33 mmol) and a 2.0M solution of ammonia in methanol (Aldrich, 15.0 ml, 30.0 mmol) was stirred and heated at a bath temperature between 50 and 60° C. in a microreactor overnight. After cooling, the reaction mixture was concentrated in vacuo to give a white solid (64.0 mg). This was purified by preparative TLC [Merck Kieselgel 60, Art 1.05744, 0.5 mm thick, x2; development: $CH_2Cl_2$—MeOH (8:1); elution: $CH_2Cl_2$—MOH (3:1), 240 ml]. The recovered white solid residue was suspended in THF, and the mixture was filtered through a short pad of Celite. The filter cake was washed with THF. The combined filtrate and washings were concentrated in vacuo to give 5-(1,2-dihydroxypropyl)-2-pyridinecarboxamide as a white solid (70.7 mg, quantitative): $^1$H-NMR (270 MHz) δ(CDCl$_3$+DMSO-d$_6$) 8.57 (d, J=2.2 Hz, 1H), 8.11 (d, J=8.1 Hz, 1H), 7.89 (dd, J=8.1, 2.1 Hz, 1H), 7.86 (br.s, 1H), 6.71 (br.s, 1H), 4.98 (d, J=4.3 Hz, 1H), 4.67 (dd, J=4.3, 4.3 Hz, 1H), 4.00 (d, J=5.1 Hz, 1H), 4.00~3.87 (m, 1H), 1.07 (d, J=6.2 Hz, 3H) ppm; MS m/z 197 (0.83%, M$^+$+1), 152 (100%).

Example Six

Preparation of 5-(1,2-dihydroxypropyl)-N,N-dimethyl-2-pyridinecarboxamide

A mixture of methyl 5-(1,2-dihydroxypropyl)-2-pyridinecarboxylate (52.0 mg, 0.25 mmol) and a 2.0M solution of dimethylamine in methanol (Aldrich, 15.0 ml, 30.0 mmol) was stirred and heated at a bath temperature of 100° C. in a microreactor for four nights. After cooling, the reaction mixture was concentrated in vacuo. The residue (60.3 mg) was purified by preparative TLC [Merck Kieselgel 60, Art 1.05744, 0.5 mm thick, x2; development: $CH_2Cl_2$—MeOH (8:1); elution: $CH_2Cl_2$—MOH (3:1), 240 ml]. The recovered white solid residue was suspended in THF, and the mixture was filtered through a short pad of Celite. The filter cake was washed with THF. The combined filtrate and washings were concentrated in vacuo to give 5-(1,2-dihydroxypropyl)-N,N-dimethyl-2-pyridinecarboxamide as a white solid (45.2 mg, 80.6%): $^1$H-NMR (270 MHz) δ(CDCl$_3$): 8.41 (d, J=1.8 Hz, 1H), 7.76 (dd, J=7.9, 1.8 Hz, 1H), 7.52 (d, J=7.9 Hz, 1H), 4.86 (d, J=3.7 Hz, 1H), 4.11~3.97 (m, 1H), 3.80 (br.s, 1H), 3.13 (s, 3H), 3.04 (s, 3H), 2.68 (br.s, 1H), 1.15 (d, J=6.6 Hz, 3H) ppm; MS m/z: 225 (7.9%, M$^+$+1), 224 (50.9%, M$^+$), 153 (100%).

Example Seven

Preparation of 5-(1,2-dihydroxypropyl)-2-pyridinecarbonitrile

To a solution of 5-(1,2-dihydroxypropyl)-2-pyridinecarboxamide (29.5 mg, 0.142 mmol) in DMF (2 ml) were added 2-methoxypropene (41 ml, 0.425 mmol) and p-toluenesulfonic acid monohydrate (4.9 mg, 0.0283 mmol) at room temperature. After stirring at room temperature for 70 min, the mixture was basified with NaHCO$_3$. The mixture was diluted with ethyl acetate (30 ml), washed with water (20 ml×2), and dried over Na$_2$SO$_4$. After the solvent was evaporated in vacuo, the oily residue was purified by preparative TLC [acetone/hexane (½, v/v)] to afford 16.4 mg (49%) of 5-(1,2-dihydroxypropyl)-2-pyridinecarboxamide as a white solid: $^1$H-NMR (270 MHz, CDCl$_3$) δ 8.49 (1 H, d, J=1.8 Hz), 8.20 (1 H, d, J=8.1 Hz), 7.84 (1 H, br s), 7.80 (1 H, dd, J=1.8 and 8.1 Hz), 5.89 (1 H, br s), 5.27 (1 H, d, J=7.0 Hz), 4.66 (1 H, quint, J=6.5 Hz), 1.66 and 1.49 (each 3 H, 2 s), 0.82 (3 H, d, J=6.5 Hz) ppm.

To a stirred solution of 5-(2,2,5-trimethyl-1,3-dioxolan-4-yl)-2-pyridinecarboxamide (16.4 mg, 0.0695 mmol) in 1,4-dioxane (1 ml) were added pyridine (23 ml, 0.278 mmol) and trifluoroacetic anhydride (20 ml, 0.139 mmol) at room temperature. After stirring at room temperature for 1 h, the mixture was diluted with ethyl acetate (20 ml), washed with sat. NaHCO$_3$ (10 ml×2), dried over Na$_2$SO$_4$, and concentrated in vacuo to give a brown syrup. This was purified by preparative TLC [acetone/hexane (¼, v/v)] to afford 9.7 mg (64%) of 5-(2,2,5-trimethyl-1,3-dioxolan-4-yl)-2-pyridinecarbonitrile as a solid: $^1$H-NMR (270 MHz, CDCl$_3$) δ 8.62 (1 H, d, J=1.8 Hz), 7.80 (1 H, dd, J=1.8 and 8.1 Hz), 7.70 (1 H, d, J=8.1 Hz), 5.25 (1 H, d, J=7.0 Hz), 4.67 (1 H, quit. J=6.6 Hz), 1.64 and 1.48 (each 3H, 2 s), 0.82 (3 H, d, J=6.6 Hz) ppm.

A mixture of (3) (9.7 mg, 0.0444 mmol) and 80% aq. acetic acid (2 ml) was stirred and heated at 60° C. for 2.5 h. The mixture was concentrated in vacuo to give a syrup. This was purified by preparative TLC [methanol/dichloromethane (⅒)] to afford 7.4 mg (94%) of 5-(1,2-dihydroxypropyl)-2-pyridinecarbonitrile: $^1$H-NMR (270 MHz, CDCl$_3$) δ 8.68 (1 H, d, J=2.2 Hz), 7.91 (1 H, dd, J=2.2 and 8.1 Hz), 7.70 (1 H, d, J=8.1 Hz), 4.84 (1 H, d, J=3.7 Hz), 4.11 (1 H, dt, J=6.2, 6.2, and 10.3 Hz), 2.99 (1 H, br s), 2.31 (1 H, br s), 1.06 (3 H, d, J=6.2 Hz) ppm.

Example Eight

Preparation of 5-(1, 2-di-hydroxypropyl)-2-(2-methyl-2H-1,2,3,4-tetrazol-5-yl)pyridine and 5-(1, 2-di-hydroxypropyl)-2-(1-methyl-1H-1,2,3,4-tetrazol-5-yl)pyridine To a solution of 5-(1,2-dihydroxypropyl)-2-pyridinecarboxamide (161 mg, 0.771 mmol) in DMF (6 ml) were added imidazole (1.05 g, 15.4 mmol) and t-butylchlorodimethylsilane (1.16 g, 7.71 mmol) at room temperature. After the mixture was stirred and heated at 70° C. for 5.5 h, water (2 ml) was added, and the stirring was continued under the same heating conditions for 2 h. The mixture was diluted with ethyl acetate (200 ml), washed with water (100 ml×4), dried over Na$_2$SO$_4$, and concentrated in vacuo to give a crystalline residue. This was chromatographed on silica gel (20 g). Elution with ethyl acetate/hexane (¼, v/v) afforded 326 mg (99%) of 5-[1,2-di-{(1-(tert-butyl)-1,1-dimethylsilyloxy}propyl]-2-pyridinecarboxamide as a white solid: $^1$H-NMR (270 MHz, CDCl$_3$) δ 8.50 (1 H, d, J=1.8 Hz), 8.15 (1 H, d, J=8.1 Hz), 7.86 (1 H, br s), 7.81 (1 H, dd, J=2.2 and 8.1 Hz), 5.89 (1 H, be s), 4.40 (1 H, d, J=6.6 Hz), 3.74 (1 H, quint., J=6.1 Hz) 1.23 (3 H, d, J=6.2 Hz), 0.87 and 0.75 (each 9 H, 2 s), 0.06, −0.11, −0.18, and −0.40 (each 3H, 4 s) ppm.

To a stirred solution of 5-[1,2-di-{(1-(tert-butyl)-1,1-dimethylsilyloxy}propyl]-2-pyridinecarboxamide (326 mg, 0.769 mmol) in 1,4-dioxane (8 ml) were added pyridine (0.25 ml, 3.07 mmol) and trifluoroacetic anhydride (0.22 ml, 1.54 mmol) at room temperature. After stirring at room temperature for 0.5 h, the mixture was diluted with ethyl acetate (100 ml), washed with sat. NaHCO$_3$ (50 ml×2), dried over Na$_2$SO$_4$, and concentrated in vacuo to give an oily residue. This was chromatographed on silica gel (30 g). Elution with ethyl acetate/hexane (⅟₁₅, v/v) afforded 264 mg of 5-[1,2-di-{(1-(tert-butyl)-1,1-dimethylsilyloxy}propyl]-2-pyridinecarbonitrile as a solid: $^1$H-NMR (270 MHz, CDCl$_3$) δ 8.65 (1 H, d, J=1.8 Hz), 7.80 (1 H, dd, J=1.8 and 7.7 Hz), 7.65 (1 H, d, J=7.7 Hz), 4.39 (1 H, d, J=6.6 Hz), 3.72 (1 H, quint., J=6.2 Hz), 1.22 (3 H, d, J=6.2 Hz), 0.88 and 0.75 (each 9 H, 2 s), 0.07, 4.08, −0.18, and −0.38 (each 3 H, 4 s) ppm.

To a solution of 5-[1,2-di-{(1-(tert-butyl)-1,1-dimethylsilyloxy}propyl]-2-pyridinecarbonitrile (191 mg, 0.468 mmol) in toluene (4 ml) were added NaN$_3$ (122 mg, 1.87 mmol) and tributyltin chloride (0.51 ml, 1.87 mmol) at room temperature. The stirring was continued with heating at reflux for 27 h. After the mixture was diluted with toluene (2 ml), 1M NaOH (2.4 ml) and MeI (0.6 ml, 9.37 mmol) were added at room temperature. After stirring at room temperature for 3 h, the mixture was diluted with ethyl acetate (100 ml), washed with water (50 ml×3), dried over Na$_2$SO$_4$, and concentrated in vacuo to give an oily residue. This was purified by preparative TLC [acetone/hexane (⅕, v/v)] to afford 149 mg (68%) of 5-[1,2-di-{(1-(tert-butyl)-1,1-dimethylsilyloxy}propyl]-2-(2-methyl-2H-1,2,3,4-tetrazol-5-yl)pyridine: $^1$H-NMR (270 MHz, CDCl$_3$) δ 8.64 (1H, d, J=1.8 Hz), 8.31 (1 H, d, J=8.4 Hz), 7.88 (1 H, dd, J=1.8 and 8.4 Hz), 4.58 (3 H, s), 4.42 (1 H, d, J=7.0 Hz), 3.77 (1 H, quint, J=6.2 Hz), 1.26 (3 H, d, J=6.2 Hz), 0.90 (and 0.76 (each 9 H, 2 s), 0.09, −0.07, −0.15, and −0.37 (each 3 H, 4 s) ppm; and 63 mg (29%) of 5-[1,2-di-{(1-(tert-butyl)-1,1-dimethylsilyloxy}propyl]-2-(1-methyl-1H-1,2,3,4-tetrazol-5-yl)pyridine: $^1$H-NMR (270 MHz, CDCl$_3$) δ 8.72 (1 H, d, J=1.8 Hz), 8.19 (1 H, d, J=8.1 Hz), 7.82 (1 H, dd, J=2.2 and 8.1 Hz), 4.45 (3 H, s), 4.41 (1 H, d, J=6.6 Hz), 3.79 (1 H, quint, J=6.2 Hz), 1.23 (3 H, d, J=6.2 Hz), 0.88 and 0.75 (each 9 H, 2 s), 0.07, −0.09, −0.17, and −0.36 (each 3 H, 4 s) ppm.

To a solution of 5-[1,2-di-{(1-(tert-butyl)-1,1-dimethylsilyloxy}propyl]-2-(2-methyl-2H-1,2,3,4-tetrazol-5-yl)pyridine (149 mg, 0.320 mmol) in THF (4 ml) were added acetic acid (73 ml, 1.28 mmol) and 1M tetrabutylammoium fluoride (TBAF) (1.3 ml, 1.28 mmol) at room temperature. After stirring for 2.5 h, the mixture was concentrated in vacuo to give a syrupy residue. This was purified by preparative TLC [acetone/hexane (⅓, v/v)] to give 42 mg (56%) of 5-(1, 2-dihydroxypropyl)-2-(2-methyl-2H-1,2,3,4-tetrazol-5-yl)pyridine: $^1$H-NMR (270 MHz, CDCl$_3$) δ 8.68 (1 H, d, J=1.8 Hz), 8.19 (1 H, d, J=8.1 Hz), 7.93 (1 H, dd, J=2.0 and 8.2 Hz), 4.85 (1 H, d, J=3.7 Hz), 4.47 (3 H, s), 4.19–4.11 (1 H, m), 3.99 (1 H, br s), 3.27 (1 H, br s), 1.09 (3 H, d, J=6.2 Hz) ppm.

To a solution of 5-[1,2-di-{(1-(tert-butyl)-1,1-dimethylsilyloxy}propyl]-2-(1-methyl-1H-1,2,3,4-tetrazol-5-yl)pyridine (76.1 mg, 0.164 mmol) in THF (3 ml) were added acetic acid (38 ml, 0.656 mmol) and 1M TBAF (0.7 ml, 0.656 mmol) at room temperature. After stirring at room temperature for 2 h, the mixture was concentrated in vacuo to give a syrupy residue. This was purified by preparative TLC [acetone/hexane (⅓, v/v)] to give 24 mg (63%) of 5-(1, 2-di-hydroxypropyl)-2-(1-methyl-1H-1,2,3,4-tetrazol-5-yl) pyridine: $^1$H-NMR (270 MHz, CDCl$_3$) δ 8.69 (1 H, d, J=2.0 Hz), 8.14 (1 H, d, J=8.1 Hz), 7.89 (1 H, dd, J=2.0 and 8.1 Hz), 4.85 (1 H, d, J=3.7 Hz), 4.44 (3 H, s), 4.17–4.08 (1 H, m), 3.83 (1 H, br s), 3.13 (1 H, br s), 1.07 (3 H, d, J=6.2 Hz) ppm.

The chemical structure of the compounds prepared in the examples are ed in the following Table.

TABLE (I)

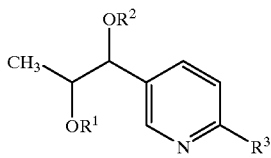

| Example Number | $R^1$ | $R^2$ | $R^3$ |
|---|---|---|---|
| 1 | H | H | $CH_3$—O—C(O)— |
| 1 | $CH_3C(O)$— | H | $CH_3$—O—C(O)— |
| 2 | H | H | COOH |
| 3 | $CH_3C(O)$— | $CH_3C(O)$— | $CH_3$—O—C(O)— |
| 4 | 4-Br-C$_6$H$_4$-C(O)— | 4-Br-C$_6$H$_4$-C(O)— | $CH_3$—O—C(O)— |
| 5 | H | H | $CONH_2$ |
| 6 | H | H | $CON(CH_3)_2$ |
| 7 | H | H | CN |
| 8 | H | H | 2-methyltetrazol-5-yl |
| 8 | H | H | 1-methyltetrazol-5-yl |

We claim:

1. A compound of formula (I):

(I)

or a pharmaceutically acceptable salt thereof, wherein $R^1$ and $R^2$ are independently H, $C_2$–$C_6$ acyl or halo-substituted benzoyl; and $R^3$ is —C(O)O—$C_1$–$C_6$ alkyl, C(O)OH, CN, $CONH_2$, $CONHCH_3$, $CON(CH_3)_2$, 1-methyltetrazole or 2-methyltetrazole, with the proviso that when $R^2$ is acetyl and $R^3$ is methoxycarbonyl, $R^1$ is not H; and that when $R^3$ is CN, $CONH_2$, $CONHCH_3$, $CON(CH_3)_2$, 1-methyltetrazole or 2-methyltetrazole, $R^1$ and $R^2$ are H.

2. A compound according to claim 1, wherein $R^3$ is —C(O)O—$C_1$–$C_6$ alkyl or C(O)OH, with the proviso that when $R^2$ is acetyl and $R^3$ is methoxycarbonyl, $R^1$ is not H.

3. A compound according to claim 2, said compound being one of the following:
a compound of formula (I) wherein $R^1$ and $R^2$ are H; and $R^3$ is methoxycarbonyl,
a compound of formula (I) wherein $R^1$ is acetyl; $R^2$ is H; and $R^3$ is methoxycarbonyl,
a compound of formula (I) wherein $R^1$ and $R^2$ are H; and $R^3$ is C(O)OH,
a compound of formula (I) wherein $R^1$ and $R^2$ are acetyl; and $R^3$ is methoxycarbonyl; and
a compound of formula (I) wherein $R^1$ and $R^2$ are p-bromobenzoyl; and $R^3$ is methoxycarbonyl.

4. A compound according to claim 3, said compound being one of the following:
a compound of formula (I) wherein $R^1$ and $R^2$ are H; and $R^3$ is methoxycarbonyl,
a compound of formula (I) wherein $R^1$ is acetyl; $R^2$ is H; and $R^3$ is methoxycarbonyl,
a compound of formula (I) wherein $R^1$ and $R^2$ are H; and $R^3$ is C(O)OH, and
a compound of formula (I) wherein $R^1$ and $R^2$ are acetyl; and $R^3$ is methoxycarbonyl.

5. A compound according to claim 3, wherein $R^1$ and $R^2$ are H, and $R^3$ is methoxycarbonyl, or $R^1$ is acetyl, $R^2$ is H, and $R^3$ is methoxycarbonyl.

6. A compound according to claim 1, wherein $R^1$ and $R^2$ are H; and $R^3$ is CN, $CONH_2$, $CONHCH_3$, $CON(CH_3)_2$, 1-methyltetrazole or 2-methyltetrazole.

7. A compound according to claim 6, wherein $R^3$ is $CONH_2$, $CON(CH_3)_2$, CN, 1-methyltetrazole or 2-methyltetrazole.

8. A pharmaceutical composition for use in the treatment of IL-1 and/or TNF mediated diseases and inhibition of IL-1 and/or TNF production, which comprises a compound according to claim 4, or a pharmaceutically acceptable salt thereof in an amount effective in such treatments; and a pharmaceutically acceptable carrier.

* * * * *

UNITED STATES PATENT AND TRADEMARK OFFICE
CERTIFICATE OF CORRECTION

PATENT NO : 6,034,107
DATED : March 7, 2000
INVENTOR(S) : Hideo Hirai; Katsuomi Ichikawa; Nakao Kojima; Hiroyuki Nishida; Kunio Satake; Nobuji Yoshikawa, all of Aichi-ken, Japan It is certified that error appears in the above-identified patent and that said Letters Patent are hereby corrected as shown below:

On the title page, add the priority line as follows:

-- Priority: November 4, 1997

Signed and Sealed this

Eighth Day of May, 2001

*Attest:*

NICHOLAS P. GODICI

*Attesting Officer*   *Acting Director of the United States Patent and Trademark Office*